(12) United States Patent
Sievert et al.

(10) Patent No.: US 7,087,788 B2
(45) Date of Patent: Aug. 8, 2006

(54) FLUOROSULFONE COMPOUNDS

(75) Inventors: Allen C. Sievert, Elkton, MD (US);
Mario J. Nappa, Newark, DE (US);
Velliyur Nott Mallikarjuna Rao,
Wilmington, DE (US); **Paul R.
Resnick**, Cary, NC (US)

(73) Assignee: **E.I. du Pont de Nemours and
Company**, Wilmington, DE (US)

( * ) Notice: Subject to any disclaimer, the term of this patent is extended or adjusted under 35 U.S.C. 154(b) by 10 days.

(21) Appl. No.: 10/916,355

(22) Filed: Aug. 11, 2004

(65) Prior Publication Data
US 2005/0082509 A1    Apr. 21, 2005

Related U.S. Application Data

(60) Provisional application No. 60/494,720, filed on Aug. 11, 2003.

(51) Int. Cl.
*C07C 315/00*    (2006.01)
*C07C 317/00*    (2006.01)
(52) U.S. Cl. .............................. 568/35; 568/32; 568/28
(58) Field of Classification Search ................ 568/35, 568/32, 28
See application file for complete search history.

(56) References Cited

FOREIGN PATENT DOCUMENTS

| GB | 1189561 | * | 2/1968 |
| GB | 2 370 768 A | | 7/2002 |
| WO | WO 01/05468 A2 | | 1/2001 |

OTHER PUBLICATIONS

Mahadevan et al., Facile Synthesis of Allyl, g-Iodoalkyl, and Cyclopropyl mTriflones via Radical-Mediated Atom-Transfer Addition of Iodomethyl Triflone to Olefins and Acetylenes, J. Am. Chem. Soc., 1995, 117, 3272-3273.*
Cherkasova et al., Synthesis of some Derivatives of Alkyl Trifluoromethyl Sulfones, Izvestiya Akademii Nauk SSSR, Seriya Khimicheskaya, 1983, 5, 1125-1130.*
Knunyants et al., Trifluoromethyl Vinyl Sulfoxide and Trifluoromethyl Vinyl Sulfone, Zhurnal Obshchei Khimii, 1967, 337 (6), 1277-1281.*

* cited by examiner

*Primary Examiner*—Johann Ritcher
*Assistant Examiner*—Chukwuma Nwaonicha
(74) *Attorney, Agent, or Firm*—James E. Shipley; Daniel M. Maloney

(57) ABSTRACT

The present invention relates to new fluorosulfone compounds. These fluorosulfone compounds have utility in preventing, controlling and extinguishing fire.

57 Claims, No Drawings

FLUOROSULFONE COMPOUNDS

CROSS REFERENCE(S) TO RELATED APPLICATION(S)

This application claims the priority benefit of U.S. Provisional Application No. 60/494,720, filed Aug. 11, 2003.

BACKGROUND OF THE INVENTION

1. Field of the Invention

The present invention relates to new fluorosulfone compounds. These fluorosulfone compounds have utility in preventing, controlling and extinguishing fire.

2. Description of Related Art

Numerous agents and methods of fire fighting are known and can be selected for a particular fire, depending upon factors such as its size, location and the type of combustible materials involved. Halogenated hydrocarbon fire fighting agents have traditionally been utilized in flooding applications protecting fixed enclosures (e.g., computer rooms, storage vaults, telecommunications switching gear rooms, libraries, document archives, petroleum pipeline pumping stations, and the like), or in streaming applications requiring rapid extinguishing (e.g., military aircraft, commercial hand-held extinguishers). Such extinguishing agents are not only effective but, unlike water, also function as "clean extinguishing agents," causing little, if any, damage to the enclosure or its contents.

The most commonly-used halogenated hydrocarbon extinguishing agents have been the bromine-containing compounds bromotrifluoromethane ($CF_3Br$, Halon™1301) and bromochlorodifluoromethane ($CF_2ClBr$, Halon™1211). These bromine-containing halocarbons are highly effective in extinguishing fires and can be dispensed either from portable streaming equipment or from an automatic room flooding system activated either manually or by some method of fire detection. However, these compounds have been linked to ozone depletion. The Montreal Protocol and its attendant amendments have mandated that Halon™1211 and 1301 production be discontinued.

Thus, there is a need in this field for substitutes or replacements for the commonly-used, bromine-containing fire extinguishing agents. Such substitutes should have a low ozone depletion potential; should have the ability to extinguish, control, and prevent fires, e.g., Class A (trash, wood, or paper), Class B (flammable liquids or greases), and/or Class C (electrical equipment) fires; and should be "clean extinguishing agents," i.e., be electrically non-conducting, volatile or gaseous, and leave no residue upon use. Preferably, substitutes will also be low in toxicity, not form flammable mixtures in air, have acceptable thermal and chemical stability for use in extinguishing applications, and have short atmospheric lifetimes and low global warming potentials.

BRIEF SUMMARY OF THE INVENTION

The aforementioned objectives of substitutes or replacements for the commonly-used, bromine-containing fire extinguishing agents are met by the present invention which comprises new fluorosulfones having utility in fighting fire.

DETAILED DESCRIPTION OF THE INVENTION

Fluorosulfones of the present invention include trifluoromethyl sulfones, pentafluoroethyl sulfones, and heptafluoroisopropyl sulfones represented by the formula $R_fSO_2C_aH_bX_cF_d$, wherein: RF is selected from the group consisting of $CF_3$, $C_2F_5$, and $CF(CF_3)_2$; X is selected from the group consisting of Cl, Br and I, preferably Br; a is 1, 2 or 3, preferably 1 or 2; b is 0 or 1; c is 0, 1 or 2, preferably 1; d is 0 or an integer from 1 to 5; b+c+d=2a+1; and b+c≧1; with the proviso that $CF_3SO_2CCl_2CF_3$ is not included.

Representative trifluoromethyl sulfones include $CF_3SO_2CHF_2$, $CF_3SO_2CClF_2$, $CF_3SO_2CBrF_2$, $CF_3SO_2CF_2I$, $CF_3SO_2CHClCF_3$, $CF_3SO_2CHFCBrF_2$, $CF_3SO_2CClFCClF_2$, $CF_3SO_2CBrFCBrF_2$, $CF_3SO_2CFICF_3$, and $CF_3SO_2CF_2CF_2I$.

These trifluoromethylsulfones may be prepared by reaction of a fluoro(halo)(hydro)sulfonyl fluoride with a source of $CF_3$ anion such as $CF_3Si(CH_3)_3$ in the presence of fluoride ion as described by Patel et al. in *Inorganic Chemistry*, (1992), v. 31, p. 2537.

For example, $CF_3SO_2CHF_2$ may be prepared by reacting $FSO_2CHF_2$ with $CF_3Si(CH_3)_3$ in the presence of fluoride, $CF_3SO_2CClF_2$ may be prepared by reacting $FSO_2CClF_2$ with $CF_3Si(CH_3)_3$ in the presence of fluoride, $CF_3SO_2CBrF_2$ may be prepared by reacting $FSO_2CBrF_2$ with $CF_3Si(CH_3)_3$ in the presence of fluoride, $CF_3SO_2CF_2I$ may be prepared by reacting $FSO_2CF_2I$ with $CF_3Si(CH_3)_3$ in the presence of fluoride, $CF_3SO_2CHClCF_3$ may be prepared by reacting $FSO_2CHClCF_3$ with $CF_3Si(CH_3)_3$ in the presence of fluoride, $CF_3SO_2CHFCBrF_2$ may be prepared by reacting $FSO_2CHFCBrF_2$ with $CF_3Si(CH_3)_3$ in the presence of fluoride, $CF_3SO_2CClFCClF_2$ may be prepared by reacting $FSO_2CClFCClF_2$ with $CF_3Si(CH_3)_3$ in the presence of fluoride, $CF_3SO_2CBrFCBrF_2$ may be prepared by reacting $FSO_2CBrFCBrF_2$ with $CF_3Si(CH_3)_3$ in the presence of fluoride, $CF_3SO_2CFICF_3$ may be prepared by reacting $FSO_2CFICF_3$ with $CF_3Si(CH_3)_3$ in the presence of fluoride, and $CF_3SO_2CF_2CF_2I$ may be prepared by reacting $FSO_2CF_2CF_2I$ with $CF_3Si(CH_3)_3$ in the presence of fluoride.

Representative pentafluoroethyl sulfones include $CF_3CF_2SO_2CHF_2$, $CF_3CF_2SO_2CClF_2$, $CF_3CF_2SO_2CBrF_2$, $CF_3CF_2SO_2CF_2I$, $CF_3CF_2SO_2CHClCF_3$, $CF_3CF_2SO_2CHFCBrF_2$, $CF_3CF_2SO_2CCl_2CF_3$, $CF_3CF_2SO_2CClFCClF_2$, $CF_3CF_2SO_2CBrFCBrF_2$, $CF_3CF_2SO_2CFICF_3$, and $CF_3CF_2SO_2CF_2CF_2I$.

These pentafluoroethyl sulfones may be prepared by reaction of an appropriate sulfonyl fluoride with tetrafluoroethylene in the presence of fluoride in an anhydrous polar solvent by a process similar to that described by Temple in *Journal of Organic Chemistry*, (1968), v.33, p.344, and French patent application no. 1,555,130.

For example, $CF_3CF_2SO_2CHF_2$ may be prepared by reacting $FSO_2CHF_2$ with tetrafluoroethylene in the presence of fluoride, $CF_3CF_2SO_2CClF_2$ may be prepared by reacting $FSO_2CClF_2$ with tetrafluoroethylene in the presence of fluoride, $CF_3CF_2SO_2CBrF_2$ may be prepared by reacting $FSO_2CBrF_2$ with tetrafluoroethylene in the presence of fluoride, $CF_3CF_2SO_2CF_2I$ may be prepared by reacting $FSO_2CF_2I$ with tetrafluoroethylene in the presence of fluoride, $CF_3CF_2SO_2CHClCF_3$ may be prepared by reacting $FSO_2CHClCF_3$ with tetrafluoroethylene in the presence of fluoride, $CF_3CF_2SO_2CHFCBrF_2$ may be prepared by reacting $FSO_2CHFCBrF_2$ with tetrafluoroethylene in the presence of fluoride, $CF_3CF_2SO_2CCl_2CF_3$ may be prepared by reacting $FSO_2CCl_2CF_3$ with tetrafluoroethylene in the presence of fluoride, $CF_3CF_2SO_2CClFCClF_2$ may be prepared by reacting $FSO_2CClFCClF_2$ with tetrafluoroethylene in the presence of fluoride, $CF_3CF_2SO_2CBrFCBrF_2$ may be prepared by reacting $FSO_2CBrFCBrF_2$ with tetrafluoroethylene in the presence of fluoride, $CF_3CF_2SO_2CFICF_3$ may be prepared by reacting $FSO_2CFICF_3$ with tetrafluoroethylene in the presence of fluoride, and $CF_3CF_2SO_2CF_2CF_2I$ may be prepared by reacting $FSO_2CF_2CF_2I$ with tetrafluoroethylene in the presence of fluoride.

Representative heptafluoroisopropyl sulfones include $(CF_3)_2CFSO_2CHF_2$, $(CF_3)_2CFSO_2CClF_2$, $(CF_3)_2CFSO_2CBrF_2$, $(CF_3)_2CFSO_2CF_2I$, $(CF_3)_2CFSO_2CHClCF_3$, $(CF_3)_2CFSO_2CHFCBrF_2$, $(CF_3)_2CFSO_2CCl_2CF_3$, $(CF_3)_2CFSO_2CClFCClF_2$, $(CF_3)_2CFSO_2CBrFCBrF_2$, $(CF_3)_2CFSO_2CFICF_3$ and $(CF_3)_2CFSO_2CF_2CF_2I$.

These heptafluoroisopropyl sulfones may be prepared by reaction of an appropriate sulfonyl fluoride with hexafluoropropene in the presence of fluoride in an anhydrous polar solvent by a process similar to that described by Temple in *Journal of Organic Chemistry*, (1968), v.33, p.344, and French patent application no. 1,555,130.

For example, $(CF_3)_2CFSO_2CHF_2$ may be prepared by reacting $FSO_2CHF_2$ with hexafluoropropene in the presence of fluoride, $(CF_3)_2CFSO_2CClF_2$ may be prepared by reacting $FSO_2CClF_2$ with hexafluoropropene in the presence of fluoride, $(CF_3)_2CFSO_2CBrF_2$ may be prepared by reacting $FSO_2CBrF_2$ with hexafluoropropene in the presence of fluoride, $(CF_3)_2CFSO_2CF_2I$ may be prepared by reacting $FSO_2CF_2I$ with hexafluoropropene in the presence of fluoride, $(CF_3)_2CFSO_2CHClCF_3$ may be prepared by reacting $FSO_2CHClCF_3$ with hexafluoropropene in the presence of fluoride, $(CF_3)_2CFSO_2CHFCBrF_2$ may be prepared by reacting $FSO_2CHFCBrF_2$ with hexafluoropropene in the presence of fluoride, $(CF_3)_2CFSO_2CCl_2CF_3$ may be prepared by reacting $FSO_2CCl_2CF_3$ with hexafluoropropene in the presence of fluoride, $(CF_3)_2CFSO_2CClFCClF_2$ may be prepared by reacting $FSO_2CClFCClF_2$ with hexafluoropropene in the presence of fluoride, $(CF_3)_2CFSO_2CBrFCBrF_2$ may be prepared by reacting $FSO_2CBrFCBrF_2$ with hexafluoropropene in the presence of fluoride, $(CF_3)_2CFSO_2CFICF_3$ may be prepared by reacting $FSO_2CFICF_3$ with hexafluoropropene in the presence of fluoride, and $(CF_3)_2CFSO_2CF_2CF_2I$ may be prepared by reacting $FSO_2CF_2CF_2I$ with hexafluoropropene in the presence of fluoride.

The present invention further includes perfluorosulfones $CF_3SO_2CF_2CF_2CF_3$, $CF_3SO_2C(CF_3)_3$, $CF_3SO_2CF_2CF(CF_3)_2$, $CF_3SO_2CF(CF_3)CF_2CF_3$, $CF_3CF_2SO_2CF_2CF_2CF_3$, $CF_3CF_2SO_2CF(CF_3)_2$, $CF_3CF_2CF_2SO_2CF(CF_3)_2$, and $(CF_3)_2CFSO_2CF(CF_3)_2$.

Perfluorosulfones $CF_3CF_2SO_2CF_2CF_2CF_3$, $CF_3SO_2CF(CF_3)CF_2CF_3$, $CF_3SO_2C(CF_3)_3$, $CF_3CF_2SO_2CF(CF_3)_2$, $CF_3CF_2CF_2SO_2CF(CF_3)_2$ and $(CF_3)_2CFSO_2CF(CF_3)_2$ may be prepared by reacting an appropriate perfluoroalkyl sulfonyl fluoride with a perfluoroolefin in the presence of fluoride in an anhydrous polar solvent by a process similar to that described by Temple in *Journal of Organic Chemistry*, (1968), v.33, p.344, and French patent application no. 1,555,130.

For example, $CF_3CF_2SO_2CF_2CF_2CF_3$ may be prepared by reacting $FSO_2CF_2CF_2CF_3$ with tetrafluoroethene in the presence of fluoride, $CF_3SO_2CF(CF_3)CF_2CF_3$ may be prepared by reacting $FSO_2CF_3$ with perfluoro-2-butene in the presence of fluoride, $CF_3SO_2C(CF_3)_3$ may be prepared by reacting $FSO_2CF_3$ with perfluoroisobutylene in the presence of fluoride, $CF_3CF_2SO_2CF(CF_3)_2$ may be prepared by reacting $CF_3CF_2SO_2F$ with hexafluoropropene in the presence of fluoride, $CF_3CF_2CF_2SO_2CF(CF_3)_2$ may be prepared by reacting $CF_3CF_2CF_2SO_2F$ with hexafluoropropene in the presence of fluoride, and $(CF_3)_2CFSO_2CF(CF_3)_2$ may be prepared by reacting $SO_2F_2$ or $FSO_2CF(CF_3)_2$ with hexafluoropropene in the presence of fluoride.

Perfluorosulfone $CF_3SO_2CF_2CF_2CF_3$ may be prepared by the fluorination of known $CCl_3SO_2CF_2CF_2CF_3$ with HF or $SbF_3/SbCl_5$ in the liquid phase. Alternatively, $CF_3SO_2CF_2CF_2CF_3$ may be prepared by direct fluorination of known $CH_3SO_2CH_2CH_2CH_3$ using the techniques reported by Harmon et al. in *Journal of the Chemical Society, Perkin Transaction I*, (1979), p.2675.

Perfluorosulfone $CF_3SO_2CF_2CF(CF_3)_2$ can be made using the techniques disclosed by Haszeldine, et.al. in *Journal of the Chemical Society, Perkin Transaction I*, (1972), p.2180, beginning with diisobutyl disulfide and trifluoromethyl iodide. The resulting trifluoromethyl isobutylsulfide may then be oxidized to the sulfone as disclosed by Haszeldine in U.S. Pat. No. 3,816,277, and finally perfluorinated according to the methods of Harmon et al. in *Journal of the Chemical Society, Perkin Transaction I*, (1979), p.2675.

The present invention further includes hydrofluorosulfones $CF_3CH_2SO_2CF_2CF_3$, $CF_3CH_2SO_2CF(CF_3)_2$, and $CH_3SO_2CF_2CF_3$.

These hydrofluorosulfones may be prepared by reacting appropriate sulfonyl fluorides with perfluoroolefins in the presence of fluoride in an anhydrous polar solvent by the process of Temple in *Journal of Organic Chemistry*, (1968), v.33, p.344, and French patent application no. 1,555,130.

For example, $CF_3CH_2SO_2CF_2CF_3$ may be prepared by reacting $FSO_2CH_2CF_3$ with tetrafluoroethene, and $CF_3CH_2SO_2CF(CF_3)_2$ may be prepared by reacting $FSO_2CH_2CF_3$ with hexafluoropropene.

Hydrofluorosulfone $CH_3SO_2CF_2CF_3$ may be prepared by reacting $C_2F_5I$ with $CH_3SSCH_3$ followed by oxidation of the intermediate sulfide using the process described by Haszeldine, et. al. in *Journal of the Chemical Society Perkin Trans. I*, (1972), p.159.

The present invention further includes halomethyl perfluoroalkyl sulfones $CH_2ClSO_2CF_2CF_3$, $CH_2BrSO_2CF_2CF_3$, $CH_2ISO_2CF_2CF_3$, $CH_2ClSO_2CF(CF_3)_2$, $CH_2BrSO_2CF(CF_3)_2$, $CH_2ISO_2CF(CF_3)_2$, $CH_2ClSO_2CF_2CF_2CF_3$, $CH_2BrSO_2CF_2CF_2CF_3$, $CH_2ISO_2CF_2CF_3$, $CH_2BrCH_2SO_2CF_3$, $CH_2ClCH_2SO_2C_2F_5$ and $CH_2BrCH_2SO_2C_2F_5$.

These halomethyl perfluoroalkyl sulfones may be prepared by reacting a metallated methyl perfluoroalkyl sulfone with chlorine ($Cl_2$), bromine ($Br_2$), or iodine ($I_2$). The methyl perfluoroalkyl sulfone may be metallated by reaction with tert-butyl lithium or a Grignard reagent such as methyl magnesium bromide in a solvent such as ether, tetrahydrofuran, dimethoxyethane and diglyme free of compounds containing acidic hydrogen atoms (e.g., water).

For example, $CH_2XSO_2CF_2CF_3$, wherein X is Cl, Br or I, may be prepared by reacting $CH_3SO_2CF_2CF_3$ with a stoichiometric amount of tert-butyl lithium at −78° C. in anhydrous diethyl ether to form intermediate $(Li^+)(^-CH_2SO_2CF_2CF_3)$, which is then promptly reacted in the same reaction vessel with a stoichiometric amount of chlorine, bromine or iodine.

For example, $CH_2ClSO_2CF_2CF_3$ may be prepared by reacting $CH_3SO_2CF_2CF_3$ with a stoichiometric amount of tert-butyl lithium at −78° C. in anhydrous diethyl ether to form intermediate $(Li^+)(^-CH_2SO_2CF_2CF_3)$ which is then promptly reacted in the same reaction vessel with a stoichiometric amount of chlorine. The iodomethyl compounds may also be prepared by reacting trimethylsilyl iodomethane with tert-butyl lithium followed by trifluoromethanesulfonic anhydride as described by Mahadevan et al. in *Tetrahedron Letters*, (1994), v.35, p. 6025.

$CH_2BrCH_2SO_2CF_3$ and $CH_2BrCH_2SO_2C_2F_5$ may be prepared by reacting the corresponding ethyl perfluoroalkyl-sulfones with bromine in the presence of a radical initiator or UV light in a solvent such as carbon tetrachloride.

$CH_2ClCH_2SO_2C_2F_5$ may be prepared by reacting the ethyl perfluoroethyl sulfone with chlorine in the presence of UV light using a process similar to that described by Laping and Hanack in *Tetrahedron Letters*, 1979, pages 1309 to 1310.

Fluorosulfones of the present invention have utility in fire fighting as fire preventing, controlling and extinguishing agents.

The present fluorosulfones may be utilized alone, in combination with one another, or in combination with a co-fire-fighting agent or propellant selected from known fire fighting agents of the classes hydrofluorocarbons, hydrochlorofluorocarbons, perfluorocarbons, perfluoroketones, bromoperfluoroketones, perfluoropolyethers, hydrofluoropolyethers, hydrofluoroethers, chlorofluorocarbons, bromofluorocarbons, bromochlorofluorocarbons, hydrobromocarbons, iodofluorocarbons, and hydrobromofluorocarbons. Such co-agents can be chosen to enhance the fire fighting capabilities or modify the physical properties (e.g., modify the rate of introduction by serving as a propellant) of a fire fighting composition for a particular type (or size or location) of fire hazard and can preferably be utilized in ratios (of co-agent to fluorosulfone) such that the resulting composition does not form flammable mixtures in air. Such fire fighting mixtures may contain from about 10–90% by weight of at least one fluorosulfone and from about 90–10% by weight of at least one co-agent.

Of particular utility are azeotropic and azeotrope-like mixtures containing the present fluorosulfones and one or more compounds selected from the group consisting of perfluoroketones, bromoperfluoroketones and hydrofluorocarbons. Such mixtures may provide a fire fighting composition with a lower boiling point than either constituent of the mixture as well as provide a constant ratio of the components of the mixture during discharge.

The present fluorosulfones may be solids, liquids, or gases under ambient conditions, but are preferably utilized for fire preventing, controlling and extinguishing in either the liquid or the gaseous state (or both). Thus, normally solid compounds are preferably utilized after transformation to liquid and/or gas through melting, sublimation, or dissolution in a liquid co-agent. Such transformation can occur upon exposure of the compound to the heat of a fire.

Introduction of a fire controlling or extinguishing composition can generally be carried out by releasing the composition into an enclosed area surrounding a fire. Any of the known methods of introduction can be utilized provided that appropriate quantities of the composition are metered into the enclosed area at appropriate intervals. For example, a composition can be introduced by streaming, e.g., using conventional portable (or fixed) fire extinguishing equipment; by misting; or by flooding, e.g., by releasing (using appropriate piping, valves, and controls) the composition into an enclosed area surrounding a fire. The composition can optionally be combined with an inert propellant, e.g., nitrogen, argon, decomposition products of glycidyl azide polymers or carbon dioxide, to increase the rate of discharge of the composition from the streaming or flooding equipment utilized. When the composition is to be introduced by streaming or local application, fluorosulfones having normal boiling points in the range of from about 40° C. to about 130° C. (especially fluorosulfones that are liquid under ambient conditions) are preferably utilized. When the composition is to be introduced by misting, fluorosulfones having boiling points in the range of from about 40° C. to about 110° C. are generally preferred. And, when the composition is to be introduced by flooding, fluorosulfones having boiling points in the range of from about 40° C. to about 80° C. are generally preferred.

Preferably, the extinguishing composition is introduced to a fire or flame in an amount sufficient to extinguish the fire or flame. One skilled in this field will recognize that the amount of extinguishing composition needed to extinguish a particular fire will depend upon the nature and extent of the hazard. When the extinguishing composition is to be introduced by flooding, cup burner test data is useful in determining the amount or concentration of extinguishing composition required to extinguish a particular type and size of fire. The amount of fluorosulfone used to control or extinguish fire is generally an average resulting concentration of between about 1 and about 10 percent by gas volume of fluorosulfone.

The present fluorosulfones are also useful for preventing a combustible material from igniting. The present fluorosulfones thus also have utility in preventing fires or deflagration in an air-containing, enclosed area that contains combustible materials of the self-sustaining or non-self-sustaining type. Such a utility involves a process comprising the step of introducing into an air-containing, enclosed area a non-flammable fire preventing composition that is essentially gaseous that comprises at least one present fluorosulfone, the composition being introduced and maintained in an amount sufficient to prevent combustion of combustible materials in the enclosed area.

For fire prevention, fluorosulfones (and any co-agent(s) utilized) can be chosen so as to provide a composition that is essentially gaseous under use conditions. Preferred compound(s) have boiling points in the range of from about 40° C. to about 130° C. The fluorosulfone composition is introduced and maintained in an amount sufficient to prevent combustion of combustible materials in the enclosed area. The amount varies with the combustibility of the particular flammable materials present in the enclosed area. Combustibility varies according to chemical composition and according to physical properties such as surface area relative to volume, porosity, etc. The present fluorosulfones can be used to eliminate the combustion-sustaining properties of air and to thereby prevent the combustion of flammable materials (e.g., paper, cloth, wood, flammable liquids, and plastic items). The present fluorosulfones can be maintained continuously if a threat of fire is always present or can be introduced into an atmosphere as an emergency measure if a threat of fire or deflagration develops.

EXAMPLES

Example 1

Synthesis of $CF_3CF_2SO_2CF_2CF_2CF_3$ $CF_3CF_2SO_2CF_2CF_2CF_3$ is prepared by reacting $FSO_2CF_2CF_2CF_3$ with tetrafluoroethene in the presence of fluoride ion in anhydrous diethyl ether by the method of Temple in *Journal of Organic Chemistry*, (1968), v.33, p.344, and French patent application no. 1,555,130.

$FSO_2CF_2CF_2CF_3$ is prepared by the electrochemical fluorination of known $FSO_2CH_2CH_2CH_3$ by the method of Hollitzer et al. as disclosed in *Journal of Fluorine Chemistry*, (1987), v.35, no. 2, p.329.

Example 2

Fire Extinguishing Concentration of $CF_3CF_2SO_2CF_2CF_3$

The fire extinguishing concentration of $CF_3CF_2SO_2CF_2CF_3$, is determined by the NFPA Standard Cup Burner method. This method is described in NFPA 2001–2003, Annex B.

Specifically, an air stream is passed at 40 liters/minute through an outer chimney (8.5 cm. I. D. by 53 cm. tall) from a glass bead distributor at its base. A fuel cup burner (3.1 cm. O.D. and 2.15 cm. I.D.) is positioned within the chimney at 23.5 cm above the top of the bead distributor. The fire extinguishing agent is added to the air stream prior to its entry into the glass bead distributor while the air flow rate is maintained at 40 liters/minute for all tests. The air and agent flow rates are measured using calibrated rotameters.

The test is conducted by adjusting the fuel (n-heptane) level in the reservoir to bring the liquid fuel level in the cup burner just even with the ground glass lip on the burner cup. With the air flow rate maintained at 40 liters/minute, the fuel in the cup burner is ignited. The fire extinguishing agent is added in measured increments until the flame is extinguished.

The fire extinguishing concentration is determined by thermal conductivity gas chromatography. A sample of the air is taken from the chimney in a gas-tight syringe and injected into the gas chromatograph that has been calibrated for the agent.

TABLE 1

| FIRE EXTINGUISHING AGENT | FIRE EXTINGUISHING CONCENTRATION (volume % in air) |
|---|---|
| EXAMPLE | |
| $CF_3CF_2SO_2CF_2CF_3$ | 6 |
| COMPARATIVE | |
| $CF_3CHFCF_3$ (HFC-227ea) | 7.3 |
| $CF_3CHFCHF_2$ (HFC-236ea) | 10.2 |
| $CF_3CF_2CH_2Cl$ (HCFC-235cb) | 6.2 |
| $CF_4$ | 20.5 |
| $C_2F_6$ | 8.7 |
| $CF_3Br$ (Halon-1301) | 4.2 |
| $CF_2ClBr$ (Halon 1211) | 6.2 |
| $CHF_2Cl$ | 13.6 |

What is claimed is:

1. A compound represented by the formula $R_FSO_2C_aH_bX_cF_d$, wherein: $R_F$ is selected from the group consisting of $CF_3$, $C_2F_5$, and $CF(CF_3)_2$; X is selected from the group consisting of Cl, Br and I; a is 1, 2 or 3; b is 0 or 1; c is 0, 1 or 2; d is 0 or an integer from 1 to 5; b+c+d=2a+1; and b+c≧1; with the proviso that $CF_3SO_2CCl_2CF_3$ is not included.

2. A compound of claim 1 wherein X is Br; a is 1 or 2; and c is 1.

3. A compound of claim 1 which is selected from the group consisting of: $CHF_2SO_2CF_2CF_3$, $CHF_2SO_2CF(CF_3)_2$, $CF_3SO_2CHF_2$, $CF_3SO_2CClF_2$, $CF_3SO_2CBrF_2$, $CF_3SO_2CF_2I$, $CF_3SO_2CHClCF_3$, $CF_3SO_2CHFCBrF_2$, $CF_3SO_2CClFCClF_2$, $CF_3SO_2CBrFCBrF_2$, $CF_3SO_2CFICF_3$, $CF_3SO_2CF_2CF_2I$, $CF_3CF_2SO_2CHF_2$, $CF_3CF_2SO_2CClF_2$, $CF_3CF_2SO_2CBrF_2$, $CF_3CF_2SO_2CF_2I$, $CF_3CF_2SO_2CHClCF_3$, $CF_3CF_2SO_2CHFCBrF_2$, $CF_3CF_2SO_2CCl_2CF_3$, $CF_3CF_2SO_2CClFCClF_2$, $CF_3CF_2SO_2CBrFCBrF_2$, $CF_3CF_2SO_2CFICF_3$, $CF_3CF_2SO_2CF_2CF_2I$, $(CF_3)_2CFSO_2CHF_2$, $(CF_3)_2CFSO_2CClF_2$, $(CF_3)_2CFSO_2CBrF_2$, $(CF_3)_2CFSO_2CF_2I$, $(CF_3)_2CFSO_2CHClCF_3$, $(CF_3)_2CFSO_2CHFCBrF_2$, $(CF_3)_2CFSO_2CCl_2CF_3$, $(CF_3)_2CFSO_2CClFCClF_2$, $(CF_3)_2CFSO_2CBrFCBrF_2$, $(CF_3)_2CFSO_2CFICF_3$ and $(CF_3)_2CFSO_2CF_2CF_2I$.

4. A perfluorosulfone selected from the group consisting of: $CF_3SO_2CF_2CF_2CF_3$ and $CF_3SO_2CF_2CF(CF_3)_2$.

5. A hydrofluorosulfone selected from the group consisting of: $CF_3CH_2SO_2CF_2CF_3$ and $CF_3CH_2SO_2CF(CF_3)_2$.

6. A halomethyl perfluoroalkylsulfone selected from the group consisting of: $CH_2ClSO_2CF_2CF_3$, $CH_2BrSO_2CF_2CF_3$, $CH_2ISO_2CF_2CF_3$, $CH_2ClSO_2CF(CF_3)_2$, $CH_2BrSO_2CF(CF_3)_2$, $CH_2ISO_2CF(CF_3)_2$, $CH_2ClSO_2CF_2CF_2CF_3$, $CH_2BrSO_2CF_2CF_2CF_3$, $CH_2ISO_2CF_2CF_2CF_3$, $CH_2BrCH_2SO_2CF_3$, $CH_2ClCH_2SO_2C_2F_5$ and $CH_2BrCH_2SO_2C_2F_5$.

7. A compound of claim 3 which is $CHF_2SO_2CF_2CF_3$.
8. A compound of claim 3 which is $CHF_2SO_2CF(CF_3)_2$.
9. A compound of claim 3 which is $CF_3SO_2CHF_2$.
10. A compound of claim 3 which is $CF_3SO_2CClF_2$.
11. A compound of claim 3 which is $CF_3SO_2CBrF_2$.
12. A compound of claim 3 which is $CF_3SO_2CF_2I$.
13. A compound of claim 3 which is $CF_3SO_2CHClCF_3$.
14. A compound of claim 3 which is $CF_3SO_2CHFCBrF_2$.
15. A compound of claim 3 which is $CF_3SO_2CClFCClF_2$.
16. A compound of claim 3 which is $CF_3SO_2CBrFCBrF_2$.
17. A compound of claim 3 which is $CF_3SO_2CFICF_3$.
18. A compound of claim 3 which is $CF_3SO_2CF_2CF_2I$.
19. A compound of claim 3 which is $CF_3CF_2SO_2CHF_2$.
20. A compound of claim 3 which is $CF_3CF_2SO_2CClF_2$.
21. A compound of claim 3 which is $CF_3CF_2SO_2CBrF_2$.
22. A compound of claim 3 which is $CF_3CF_2SO_2CF_2I$.
23. A compound of claim 3 which is $CF_3CF_2SO_2CHClCF_3$.
24. A compound of claim 3 which is $CF_3CF_2SO_2CHFCBrF_2$.
25. A compound of claim 3 which is $CF_3CF_2SO_2CCl_2CF_3$.
26. A compound of claim 3 which is $CF_3CF_2SO_2CClFCClF_2$.
27. A compound of claim 3 which is $CF_3CF_2SO_2CBrFCBrF_2$.
28. A compound of claim 3 which is $CF_3CF_2SO_2CFICF_3$.
29. A compound of claim 3 which is $CF_3CF_2SO_2CF_2CF_2I$.
30. A compound of claim 3 which is $(CF_3)_2CFSO_2CHF_2$.
31. A compound of claim 3 which is $(CF_3)_2CFSO_2CClF_2$.
32. A compound of claim 3 which is $(CF_3)_2CFSO_2CBrF_2$.
33. A compound of claim 3 which is $(CF_3)_2CFSO_2CF_2I$.
34. A compound of claim 3 which is $(CF_3)_2CFSO_2CHClCF_3$.
35. A compound of claim 3 which is $(CF_3)_2CFSO_2CHFCBrF_2$.
36. A compound of claim 3 which is $(CF_3)_2CFSO_2CCl_2CF_3$.
37. A compound of claim 3 which is $(CF_3)_2CFSO_2CClFCClF_2$.
38. A compound of claim 3 which is $(CF_3)_2CFSO_2CBrFCBrF_2$.
39. A compound of claim 3 which is $(CF_3)_2CFSO_2CFICF_3$.
40. A compound of claim 3 which is $(CF_3)_2CFSO_2CF_2CF_2I$.

41. A compound of claim 4 which is $CF_3SO_2CF_2CF_2CF_3$.
42. A compound of claim 4 which is $CF_3SO_2CF_2CF(CF_3)_2$.
43. A compound of claim 5 which is $CF_3CH_2SO_2CF_2CF_3$.
44. A compound of claim 5 which is: $CF_3CH_2SO_2CF(CF_3)_2$.
45. A compound of claim 5 which is: $CH_3SO_2CF_2CF_3$.
46. A compound of claim 6 which is $CH_2ClSO_2CF_2CF_3$.
47. A compound of claim 6 which is $CH_2BrSO_2CF_2CF_3$.
48. A compound of claim 6 which is $CH_2ISO_2CF_2CF_3$.
49. A compound of claim 6 which is $CH_2ClSO_2CF(CF_3)_2$.
50. A compound of claim 6 which is $CH_2BrSO_2CF(CF_3)_2$.
51. A compound of claim 6 which is $CH_2ISO_2CF(CF_3)_2$.
52. A compound of claim 6 which is $CH_2ClSO_2CF_2CF_2CF_3$.
53. A compound of claim 6 which is $CH_2BrSO_2CF_2CF_2CF_3$.
54. A compound of claim 6 which is $CH_2ISO_2CF_2CF_2CF_3$.
55. A compound of claim 6 which is $CH_2BrCH_2SO_2CF_3$.
56. A compound of claim 6 which is $CH_2ClCH_2SO_2C_2F_5$.
57. A compound of claim 6 which is $CH_2BrCH_2SO_2C_2F_5$.

* * * * *